United States Patent [19]

Miller et al.

[11] Patent Number: 5,326,392
[45] Date of Patent: Jul. 5, 1994

[54] PLATY PIGMENTS

[75] Inventors: Harold A. Miller; Philip Greenberg, both of White Plains; Adolph Blum, Yorktown Heights; Wasi Ahmed, Lake Mohegan, all of N.Y.

[73] Assignee: The Mearl Corporation, Ossini, N.J.

[21] Appl. No.: 93,903

[22] Filed: Jul. 20, 1993

Related U.S. Application Data

[63] Continuation-in-part of Ser. No. 622,055, Dec. 4, 1990, abandoned.

[51] Int. Cl.$^5$ .............................................. C04B 14/20
[52] U.S. Cl. .................................. 106/417; 106/418; 106/469; 106/471; 106/486; 106/487; 106/499; 514/844
[58] Field of Search .............. 106/499, 417, 418, 469, 106/471, 486, 487; 514/844

[56] References Cited

U.S. PATENT DOCUMENTS

| | | | |
|---|---|---|---|
| 4,134,776 | 1/1979 | Rieger et al. | 106/417 |
| 4,606,914 | 8/1986 | Miyoshi | 424/63 |
| 4,622,074 | 11/1986 | Miyoshi et al. | 106/419 |
| 4,640,943 | 2/1987 | Meguro et al. | 106/414 |
| 4,863,800 | 9/1989 | Miyoshi et al. | 428/403 |
| 4,867,793 | 5/1989 | Franz et al. | 106/415 |
| 4,919,922 | 4/1990 | Miyoshi et al. | 428/407 |
| 5,091,011 | 2/1992 | DeLuca, Jr. | 106/417 |

FOREIGN PATENT DOCUMENTS

| | | |
|---|---|---|
| 0139481 | 5/1985 | European Pat. Off. |
| 58-32660 | 2/1983 | Japan |
| 61-136555 | 6/1986 | Japan |
| 63-17972 | 1/1988 | Japan |

OTHER PUBLICATIONS

Sakamoto et al. Yukagaku (Petroleum Chemistry), vol. 26, No. 2, pp. 110–114 (1977). (Translation).
Esumi et al., Bull. Chem. Soc. Japan, vol. 56, pp. 2569–2571 (1983).
Ajinimoto Co., Inc., "Amihope LL" (Brochure), pp. 1–6 and 12 (Apr. 1985).

*Primary Examiner*—Mark L. Bell
*Assistant Examiner*—Scott L. Hertzog
*Attorney, Agent, or Firm*—Ostrolenk, Faber, Gerb & Soffen

[57] ABSTRACT

Platy pigments with good tactile characteristics are obtained by treating such pigments with a compound of the general formula:

$$CH_3(CH_2)_m-\overset{O}{\underset{\|}{C}}-\underset{|}{\overset{H}{N}}-(CH_2)_n-\underset{\underset{NH_2}{|}}{\overset{H}{\underset{|}{C}}}-COOH$$

where m is an even number from 8 to 18 and n is 3 or 4 under defined conditions. Nε-lauroyl lysine is preferred. The pigments are especially useful in cosmetic compositions such as eye shadow.

36 Claims, No Drawings

PLATY PIGMENTS

This is a continuation-in-part of application Ser. No. 07/622,055 filed on Dec. 4, 1990, abandoned.

BACKGROUND OF THE INVENTION

During the past decade, attempts have been made to improve the tactile or "feel" characteristics of powders and of solid compacts intended for cosmetic makeup purposes in the eye region and on the face. The general approach has been to treat the surfaces of the major pigments in these formulations. Treatment also was intended to improve the dispersion or the compatibility of the pigment in the compact formulation.

Compact formulations containing largely platy pigments or extenders such as mica already had reasonably smooth and soft tactile properties, due to the flat or platy shape of the pigment particles. However, it was recognized that these pigments could also be improved by treatment. Talc, a platy extender frequently used in compact formulations, showed several disadvantages. The softness of talc contributed to its ease of breaking up physically so that the platy character would be substantially decreased or lost. The softness of the talc also contributed to its hard compaction when subjected to pressure, so that pay-off of the formulation in use became low.

Mica, as an extender in these compact formulations, was found to overcome some of the disadvantages of the talc. Mica, as a harder material but still platy in shape, resists being broken up physically. It also has some resistance to compaction, so that by adjusting the binder formulation of the compact, a reasonably soft compact is attainable along with good pay-off.

The outer structure of human skin is a mosaic of hydrophilic and hydrophobic areas. The best tactile effects, or the best smoothness and softness, are attained with the coating of pigment surfaces with compounds that have a hydrophile-hydrophobe balance similar to human skin, and with compounds that have some chemical relationship to skin.

Mica, as well as some of the metal oxide coated mica pigments used as pearlescent and color interference type pigments in compact and powder formulations, may have more surface hydrophilic character than is desirable for good tactile qualities on the skin. This means that the surface of the mica or of the platy pigment may have some drag in being applied to the skin. The hydrophile-hydrophobe balance of the pigment surface should be shifted. This is done with appropriate treatment of the pigment surfaces. The treatment consists of coating the surfaces of the pigment with a suitable compound. In many cases, the compounds or agents used have shifted the hydrophile-hydrophobe balance very strongly toward hydrophobic. This is neither desirable nor necessary.

Compounds that have been used for pigment surface treatment include silicones, silanes, siloxanes, fatty acids, chemically modified polyolefins, and fatty acid triglycerides (fats). These generally cause a large shift towards hydrophobic character and therefore, less than desirable tactile qualities.

Others have been used that are substantial improvements over the above group. They include amino acid derivatives, lecithin, safcosine derivatives, and others based on derivatives of natural products. The hydrophile-hydrophobe shift is modest towards hydrophobic and desirable. The tactile qualities are improved. However, in some cases, rancidity may result from the oxidation of some unsaturated fatty acid components. The solubilities of some of these compounds in components of the binder formulation may be substantial, leading to removal of some of the compound from the pigment surface. Mechanical treatment in the course of preparing the formulation for compaction may result in mechanically removing some of the treatment compound from the pigment surface. Finally, the adherence or adsorption of the treatment compound to the pigment surface is questionable, so that migration of the compound away from the pigment surface may take place with time.

European Patent Publication No. 139,481 of May 2, 1985 discloses methods for treating inorganic pigments with N-mono-acylated basic amino acids containing long chain acyl groups, e.g., Nε-lauroyl-L-lysine. The publication states that any dry or wet procedure may be used. The "dry" procedure involves dry blending of the components. A "wet" procedure involves dissolving the treatment compound in an organic solvent, using calcium chloride as a solubilizing agent, bringing the inorganic pigment into contact with the solution and then washing the mixture with water to remove calcium chloride. An alternative "wet" procedure involves dissolving the treatment compound in an aqueous alkali or an aqueous solvent, bringing the inorganic pigment into contact with the solution, neutralizing the mixture, precipitating and adhering the treatment compound to the pigment surface, washing with water and drying. It is implied that the alternative methods yield equivalent products.

Of the three methods disclosed, the dry blending method is shown in Example X, infra, not to yield a satisfactory product; the only solvent mentioned in connection with a wet method is calcium ethylate, the use of which is expensive and impractical; and the alternative wet method suggested is not disclosed with sufficient particularity to enable it to be successfully practiced.

It is an object of the invention to provide an improved method for producing a treated platy pigment with improved tactile characteristics and with good adherence of the treatment material to the pigment surface. Other objects of the invention will become apparent from the following description.

SUMMARY OF THE INVENTION

We have found that the objects of the invention may be achieved by precipitating a compound of the general formula

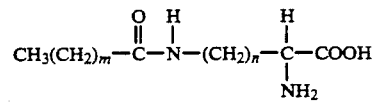

where m is an even number from 8 to 18 and n is 3 or 4, onto the surface of a platy pigment. The precipitation is accomplished by adding an acid or alkaline solution of the compound of that formula to an aqueous dispersion of the platy pigment, the Mount of the solution being such as to supply that compound in an amount of about 0.5–5.0% by weight of the pigment, at a rate not exceeding 1.50 mg. and preferably within the range of about 0.10–1.50 mg. per gram of pigment per minute, adding alkali or acid as required to bring the pH of the resulting mixture to between 1 and 8, and recovering the platy pigment coated with said compound, as by allowing it to settle, washing it, concentrating it by centrifuging or filtration and then drying it. Although racemic mixtures of the D and L forms of the compound can be used, the stereoisomeric forms wherein the structure is entirely D or L are greatly preferred for better crystallinity and greater insolubility.

The treatment is preferably carried out at a temperature between about 15° and 80° and the pH of the resulting mixture is preferably brought to about 2.5 to 5.0. It is further preferred that the treatment be carried out in the presence of a calcium salt, e.g., calcium chloride, which is suitably present in the range of about 0.25–1.0 mole per mole of treatment compound.

The preferred treatment compound is N$\epsilon$-lauroyl-L-lysine and the compound which is entirely either the D or L isomer is most preferred.

The coated platy pigment is preferably recovered by allowing it to settle, washing it, concentrating it by centrifugation or filtration and then drying it.

The resultant treated pigment is markedly improved in its tactile (or feel) characteristics, which is particularly advantageous for cosmetic formulations, especially for powder or pressed compact types in the eye region in particular, and on the skin in general.

The treatment, with some variations, is applicable to platy pigments in general, including mica, talc, titanium dioxide coated mica, iron oxide coated mica and chromium oxide coated mica. It also can be used for the more complex interference type colorants based on titanium dioxide coated mica such as those containing carmine or iron blue, as well as those containing laked forms of D&C or FD&C colorants. The disclosure in U.S. Pat. No. 4,968,351, issued Nov. 6, 1990, in respect to such pigments is hereby incorporated by reference. However, the treatment would serve little purpose applied to platy pigments which already have good tactile properties and disperse well in hydrophobic systems. An example of such pigment is bismuth oxychloride.

In the case of certain coated pigments, e.g., mica coated with iron oxide, titanium dioxide or chromium (III) oxide, the pigment is treated with a polyvalent metal compound, e.g., such as a hydroxide or a compound hydrolyzable to a hydroxide, aluminum chloride for titanium dioxide coated mica, ferric chloride for iron oxide coated mica and chromium III chloride or sulfate for chromium oxide coated mica before or during the addition of the treatment compound.

A preferred platy pigment product of this invention, which has improved tactile, dispersion and stability properties, comprises a N$\epsilon$-lauroyl-L-lysine substrate of platelets of mica, talc or metal oxide coated mica, the platelets having a particle size in the range of about 2–80 microns, and an average particle size of about 5–40 microns, the N$\epsilon$-lauroyl-L-lysine coating being present on the surface of the platelets in the range of about 0.5% to 5.0% by weight of the platelets, and at least 60% of the coating remaining adhered to the substrates after four centrifugations, each centrifugation being carried out on a dispersion of 1.00 g. of the platy pigment in 75 ml. of distilled water.

The substrate may be talc, wet ground Indian mica, iron oxide coated mica, titanium dioxide coated mica, or chromium oxide coated mica. The titanium oxide coated mica may be further coated with a dye or pigment, e.g., carmine, a laked dye or ferric ferrocyanide.

Where an organic colorant is used, it may be deposited concurrently with N$\epsilon$-lauroyl-L-lysine.

Another feature of the invention is cosmetic compositions containing the improved platy pigments in combination with cosmetically acceptable ingredients, especially powders and compacts intended for cosmetic makeup purposes in the eye region or the face, such as pressed powder eye shadow compositions.

DETAILED DESCRIPTION OF THE INVENTION

For a number of reasons, treatment with the compounds of the above given general formula, N$\epsilon$-lauroyl-L-lysine in particular, overcomes the various shortcomings of the prior art surface treatments. The following properties of N$\epsilon$-lauroyl-L-lysine are significant in distinguishing this compound from others hitherto used for pigment surface treatment: (1) It is a pure compound chemically. (2) It is stereochemically a pure compound. (3) It is very insoluble in nearly all solvents. (4) It is a distinctly crystalline compound stable up to high temperatures ($\sim 300°$ C.). A discussion of the unique character of this compound is in order.

N$\epsilon$-lauroyl-L-lysine is synthesized from lauric acid and L-lysine; both raw materials are very pure compounds. L-lysine is the result of a biological reaction, so the compound is entirely in the L-stereoisomeric form. L-lysine has 2 amino groups, one in the $\alpha$-position and the other in the $\epsilon$-position. The reaction to form N$\epsilon$-lauroyl-L-lysine is carried out so that both the reaction to form the peptide linkage is entirely with the $\epsilon$-amino group, and the stereoisomeric structure of the lysine portion is maintained.

Thus, the N$\epsilon$-lauroyl-L-lysine is obtained, a compound of specific stereostructure, high crystallinity, great stability even up to 300° C., and insoluble in nearly all solvents. The chemical structure is such that both hydrophilic and hydrophobic groups are evident. The hydrophilic groups may serve in part to assist the adsorption and crystal growth of the compound on to the mica platelet surface.

The insolubility and inertness of N$\epsilon$-lauroyl-L-lysine limits its potential for use by precipitation from solution. It is virtually insoluble in all common organic solvents. It is soluble in mineral acids. It Can be dissolved in 1.0N HCl at elevated temperature and in concentrated HCl at room temperature. Solutions in alkali are more convenient as the solubility is greater; 1.0% solutions in 0.5N NaOH are easily attainable.

Since the N$\epsilon$-lauroyl-L-lysine is insoluble in aqueous solution except under the strongly acid or alkaline conditions, the precipitation of the compound on a platy pigment can be carried out by adding either an acidic or alkaline solution of the compound to an aqueous reservoir with stirring, in which the platy pigment is dispersed. Alkali or acid is then added to bring the pH into the range of 1–8 and preferably near about 2.5–5.0. The reaction can be carried out at ambient temperature. The compound precipitates out of solution and, under the conditions of the reaction medium, on to the platy pigment surfaces. The pigment is allowed to settle, is washed several times, concentrated by centrifuging or filtration, and finally dried by any of a number of methods.

In some cases, the precipitation of the compounds is carried out with a calcium salt in the stirred aqueous reservoir. Calcium chloride is the convenient salt, present in the reservoir within the range of about 0.25–1.0 mole, preferably at about 0.5 mole, for each mole of Nε-lauroyl-L-lysine added. A salt with the compound is essentially not formed. The effect of the calcium chloride is a salting out effect. That is, the salting out may speed up or facilitate the precipitation, and it beneficially affects the character of the precipitate and the treated pigment.

The compound is deposited, at concentrations in the range of about 0.5%–5.0%, on the pigment, preferably in the concentration range of about 2.0%–4.0%.

Variables in the several procedures include pH, temperature, concentrations, and addition rates.

The mica substrate is usually a wet ground mica with particle size in the range of about 2–100 microns. Usually, for cosmetic ingredient purposes the mica is fractionated into relatively tight ranges of particle size distribution. Common ranges are 5–25 microns with 10 micron average, 1–45 microns with 20 micron average, 20–70 microns with 45 micron average, and 15–90 microns with 50 micron average. All are suitable substrates, but in terms of tactile smoothness, the larger particles within these ranges are less desirable.

The pH of the solution during lauroyl lysine addition can be varied or held constant over the range of 1–8. The preferred pH range is about 2.5–5.0, both for constant pH procedures and for procedures of variable pH starting low and ending up at pH 2.5–5.0.

Temperature is essentially not critical in that any temperature from about 15° C. to 80° C. can be used. Since there are usually no advantages at high temperatures, it is more convenient to use ambient temperatures, or about 15°–35° C., preferably about 20°–30° C.

Mica as a substrate is generally dispersed in the aqueous medium at about 20% wt./wt., before the start of the treatment reaction. The mica cannot form a good dispersion and cannot be stirred adequately if the concentration is much higher. 24% wt./wt. can be taken as about the upper limit of concentration. On the other hand, the mica can be as dilute as 4% wt./wt. There is no product quality advantage and the yield of product, based on total batch size, would be quite small. Mica concentration can therefore be in the range of about 4%–24% wt./wt., and preferably about 10%–20% wt./wt. These concentration ranges are also applicable to laked dye coated titanium dioxide coated mica. Iron oxide, titanium dioxide or chromium (III) oxide coated mica concentration can be in the range of about 5–15%, preferably about 7–12% wt./wt.

Other substrates, such as talc, are more sensitive to substrate concentration and are generally in the range of about 7.5%–10.0% wt./wt. However, any concentration within the range of about 5%–15% wt./wt. may be employed, preferably the range of about 7%–12% wt./wt.

The critical rate in all procedures is that of the lauroyl lysine solid addition rate per weight of substrate in the reservoir. These rates can be as high as 1.50 mg. and preferably within the range of about 0.10–1.50 mg. lauroyl lysine per g. substrate per minute. However, the extremes are inconvenient in that the times and/or concentrations become too high or too low for convenience. The most preferred rate range is about 0.15–1.0 mg. lauroyl lysine per g. substrate per minute.

Rates are not varied in general during the treatment procedure, so that lauroyl lysine concentration (wt. per wt. substrate) is not a factor.

The final treated powders are evaluated in three ways: tactile properties, adhesion to substrate, and dispersion properties.

Most important is tactile quality, which is determined by comparison testing on the skin, using control samples as well as the untreated pigment. Substantial improvement in smoothness and softness on the skin is to be expected, comparable to the untreated platy pigment and as good as, or slightly better than other platy pigment samples that received treatments with other compounds.

The treated platy pigment is more hydrophobic than the untreated pigment. The dispersion is improved in going to more hydrophobic solvents, i.e., butanol to butyl acetate to toluene.

The improvement in tactile character and the increased hydrophobicity depend largely on the chemical structure of the treating compound and how it is oriented on the surface of the platy pigment. While the Nε-lauroyl-L-lysine can easily be made very insoluble, nevertheless, the compound must precipitate, and adhere to the substrate pigment surface. The process of the present invention results in a high degree of adherence of the compound to the pigment surface.

It has been found that different pigment surfaces vary widely in the extent of acceptance of the treating compound to the pigment surface. Coating and adhesion to the substrate pigment surfaces can be improved by adjusting the treatment condition variables such as pH profile, salt content, rates of addition of reactants, and temperature.

In some cases, the substrate pigment surface remains unreceptive to the treating compound and appears to reject it totally. In such cases, the platy pigment requires a pretreatment with an unrelated agent to render the surfaces more receptive.

There is another category of platy pigments that would benefit from treatment with the described compound. These are the more complex interference type pigments that contain absorption colorants deposited on the platy pigment surface through a laking process. The latter involves the insolubilization of the absorption colorant and adherence to the substrate platy pigment by means of aluminum hydroxide alone, or replaced by or in conjunction with other polyvalent hydroxides of barium, calcium, zirconium, and others.

These products are sensitive to variable pH conditions in solution, and the laked color may be altered, partially removed, or otherwise damaged by the later procedure involving the deposition of Nε-lauroyl lysine or a homologue thereof. It has been found that the treatment with such compounds can be included in the laking process for the absorption colorant. These include absorption colorants such as carmine, ferric ferrocyanide, D&C colors and FD&C colors.

While the pigment treatment is limited to those of platy shape or structure, the invention is not limited to only those pigments given in the examples. While Nε-lauroyl-L-lysine is here exemplified as the treating compound, the invention is not limited to this compound, and those of related chemical structure, such as Nε-lauroyl-L-ornithine, can be used as well. The compounds which are contemplated are those of the general formula appearing above.

The process of this invention is illustrated by the following examples.

EXAMPLE I

Wet Ground Indian Mica Coated with 4.0% Nε-Lauroyl-L-Lysine

Indian mica is wet ground, followed by extensive classification by settling in water to remove fine and coarse particles. The resultant fraction has an average platelet particle size of 10 microns, and 95% of the platelets are within the range of 4–32 microns (in length).

150 g. of this mica is slurtied in 600 ml. of distilled water in a 2.0 liter beaker. 25 ml. of concentrated HCl are added and the suspension is stirred with power from a small motor, for 10 minutes. 1.68 g. of $CaCl_2.2H_2O$ are added as a solid and the suspension is stirred for 10 minutes to allow for dissolution.

A solution of 6.0 g. of Nε-lauroyl-L-lysine in 579 ml. of 0.50 Normal NaOH is prepared. This solution is added to the mica slurry at the rate of 4.8 ml. per minute until it is used up, ambient temperatures being maintained. This requires 2.0 hours in time. The final pH is 4.0, or adjusted to this pH, if necessary.

The product is filtered on a Buchner funnel, and the filtrate is washed 4 times each with 400 ml. of distilled water. The filter cake is dried in an air oven overnight at 95° C. The dried cake is screened through a 200 mesh screen.

Analyses show that practically all of the Nε-lauroyl-L-lysine has been precipitated on the mica surfaces, at 4.0%. The calcium chloride was used at 0.63 moles per mole of the Nε-lauroyl-L-lysine, yet very little calcium is found by analysis of the coated product. Thus, the calcium salt acts to reduce further the solubility of the compound used for treatment.

Settling tests in a set of organic solutions carried out with the treated mica, as well as the original untreated mica separately, shows that the treated mica displays a more hydrophobic behavior compared to the original untreated mica.

The treated mica sample, the untreated mica, and a sample of lecithin treated mica were each evaluated and compared for tactile properties. The untreated mica showed less smoothness and softness when spread on the skin, as well as a slight drag during spreading, compared to the two other samples. The Nε-lauroyl-L-lysine treatment of the mica yielded slightly better softness and smoothness compared to the lecithin treated mica.

The treated sample was subjected to an evaluation for the adhesion of the compound to the mica substrate. 100 ml. of distilled water were added to 3.0 g. of the treated mica, dispersed, centrifuged, and the supernatant liquid separated. Washing of the settled solid in this way was repeated three more times.

The sample was then analyzed for the remaining treatment compound. It was found that 92% of the treatment compound remained adhering to the mica.

Analysis of the treated mica for calcium shows that very little calcium is co-precipitated with the treatment compound, so that the calcium chloride is effecting a salting out effect on the Nε-lauroyl-L-lysine.

EXAMPLE II

Upscaled Coating of Wet Ground Indian Mica with 4.0% Nε-Lauroyl-L-Lysine

Indian wet ground mica is prepared and classified as in Example I. The Nε-lauroyl-L-lysine, 6.0 lbs., is added and dissolved in 260 lbs. of 3.50% NaOH solution. This is a 2.30% treatment solution in 3.50% NaOH.

10% HCl solution, for pH control, is prepared by adding 8.4 lbs. of 31% HCl to 17.1 lbs. of demineralized water.

800 lbs. of demineralized water are added to a 500 gallon reactor fitted with a stirrer and 2.25 lbs. of $CaCl_2.2H_2O$ are added and dissolved. 200 lbs. of the above-prepared mica are dispersed in this solution. The temperature is adjusted to 30°±1° C. and maintained at that temperature. The 3.50% NaOH solution, containing the treatment compound, is added at a rate of 4.7 lb. per minute, and the 10% HCl solution is added at about the same rate, or adjusted so as to maintain the pH at 6.0±0.1. 200 lbs. of the 3.50% NaOH solution containing 2.30% of the treatment compound are added in about 60 minutes.

The treated mica is allowed to settle, is decanted, and the liquid is replaced with an equal volume of demineralized water. After settling, the washing process is repeated. The settled paste of treated mica is dried. The product is tested in the same way as in Example I, yielding similar results.

EXAMPLE III

Wet Ground Indian Mica Coated at Constant pH to 2.0% Nε-Lauroyl-L-Lysine 225 g. of mica, prepared and classified as in Example I are dispersed in 900 ml. of distilled water. The pH is adjusted to 6.0. 5.85 g. of Nε-lauroyl-L-lysine are dissolved in 562 ml. of 0.50 Normal NaOH. This solution is added to the mica suspension, with stirring, at a rate of 6.0 ml. per minute.

The pH is maintained constant at 6.0±0.1 by simultaneous addition of 0.50 Normal HCl solution at such a rate so as to maintain the pH at 3.0, ambient temperatures being maintained. When 432 ml. of the 0.50 Normal NaOH solution has been added, the additions are halted. The slurry is filtered, washed 3 times with 400 ml. of distilled water, and dried overnight at 95° C. The product is tested in the same way as in Example I, yielding similar results.

EXAMPLE IV

Talc Treated with 3.0% Nε-Lauroyl-L-Lysine 681 g. of talc (Suprafino A, Cyrus Industrial Minerals Co.) were added to 7900 ml. of distilled water and stirred vigorously to disperse well. This dispersion was carried out in a 5 gallon polycarbonate tank, fitted with baffles, a pH electrode, and a stainless steel turbine stirrer. Ambient temperature was employed.

To this dispersion with vigorous stirring were added at 21 ml. per minute, a solution of 1.04% Nε-lauroyl-L-lysine in 1965 ml. of 0.50 Normal NaOH. The pH was maintained at 6.4±0.2 by the simultaneous addition of a solution of 0.28% $CaCl_2.2H_2O$ in 2120 ml. of 0.50 Normal HCl.

Upon completion of the addition, the slurry was stirred an additional 10 minutes and allowed to stand overnight. The next day a very small amount of material was floating on the top of the liquid, which was skimmed off. The bulk of the treated talc had settled, and this material after decantation, was filtered, washed with demineralized water and dried at 95° C. for 4 hours. The product was sieved through a 60 mesh screen.

The tactile properties were tested and found to be improved over those of the original untreated talc. Dispersion tests also showed that the treated product displayed increased hydrophobicity.

Examples I to IV, above, illustrate methods useful for treating uncomplicated substrates, such as mica, kaolin, and talc. Certain more complicated pigments such as titanium dioxide coated mica with a carmine coating may also be treated in a similar way, as shown in Example V.

EXAMPLE V

Carmine Coated Titanium Dioxide Coated Mica Additionally Coated with 3.0% N$\epsilon$-Lauroyl-L-Lysine Before carrying out the coating reaction, the solutions needed were prepared. 21.0 g. of N$\epsilon$-lauroyl-L-lysine were dissolved in 2.0 liters of 0.50 Normal NaOH. 6.72 g. of $CaCl_2.2H_2O$ were dissolved in 2400 ml. of distilled water to which had previously been added 100 ml. of concentrated HCl solution.

A 5.0 gallon polycarbonate tank was fitted with baffles and a stainless steel turbine stirrer fitted with a motor drive. To this reactor were added 7.90 liters of distilled water, and 681 g. of the pigment were added and slurried in with vigorous mixing. The pigment was Cloisonne Red of The Mearl Corporation, titanium dioxide coated mica with a carmine treatment (2.0% carmine, 39% $TiO_2$, and 59% mica). The pigment has a red interference reflection color enhanced further by the red color of the carmine colorant treatment.

At ambient temperature, the alkaline treatment solution was added at a rate of 25 ml. per minute while simultaneously maintaining the pH at 7.1±0.2 by the addition of the acidic calcium chloride solution.

When the first solution was used up, the slurry was stirred an additional 15 minutes, filtered, washed three times with small volumes of distilled water, and dried overnight at 55°–60° C.

The product was screened through a 60 mesh sieve. The testing was done as in Example I, and the tactile properties in particular were significantly improved over the original untreated pigment. Dispersion also displayed improved color intensity and luster, compared to the original untreated pigment.

Titanium dioxide coated mica, iron oxide coated mica and chromium oxide coated mica all require treatment with another compound, either before or during the lauroyl lysine addition, to effect improved adhesion to the substrate pigment surface by the lauroyl lysine. In general, a polyvalent metal hydroxide or a salt which hydrolyzes to a hydroxide during the treatment process is suitable, and the particular one selected must meet specific requirements concerning refractive index, color, and solubility. For titanium dioxide coated mica, aluminum chloride is suitable; for iron oxide coated mica, ferric chloride; and for chromium oxide coated mica, chromium (III) chloride or chromium (III) sulfate. Examples VI and VII illustrate such methods.

EXAMPLE VI

Iron Oxide Coated Mica Treated with 3.0% N$\epsilon$-Lauroyl-L-Lysine 100 g. of iron oxide coated mica pigment (Matte Orange of The Mearl Corporation, 9% $Fe_2O_3$ and 91% mica) were dispersed in 1.0 liter distilled water in a 2.0 liter beaker fitted with an appropriate mixing device. With stirring, this solution was raised to 74° C. and the pH adjusted down to 3.0 by the addition of a small amount of an acidic ferric chloride solution (2.66 g. 38% $FeCl_3$ and 97.34 g. 37% HCl solution).

Then an alkaline solution of N$\epsilon$-lauroyl-L-lysine (3.0 g. in 100 ml. of 3.5% NaOH solution) was added at 2.5 ml. per minute while maintaining the pH at 3.0±0.1 by the addition of the above acidic ferric chloride solution.

After all the N$\epsilon$-lauroyl-L-lysine solution had been added, the slurry was allowed to cool, was filtered, and washed with distilled water until the filtrate tested free of chloride. The product was dried at 80° C. overnight and sieved through a 100 mesh screen.

The ferric chloride addition results in hydrolysis to form a small amount of iron hydroxide which aids in the adhesion of the N$\epsilon$-lauroyl-L-lysine to the pigment surface.

Testing of this product for tactile properties and for dispersibility showed substantial improvements over the initial untreated pigment, Matte Orange.

EXAMPLE VII

Titanium Dioxide Coated Mica Treated with 3.0% N$\epsilon$-Lauroyl-L-Lysine 100 g. of titanium dioxide coated mica pigment (Flamenco Blue of The Mearl Corporation, 46% $TiO_2$ and 54% mica) were dispersed in 1.0 liter distilled water in a 2.0 liter vessel. With stirring, the pH was adjusted to 5.0 with 0.10 Normal HCl solution.

An alkaline solution of N$\epsilon$-lauroyl-L-lysine (3.0 g. in 100 ml. of 3.5% NaOH solution) were added at 2.5 ml. per minute while simultaneously adding a 20% solution of $AlCl_3.6H_2O$ at a rate so as to maintain the pH at 5.2±0.1. When the N$\epsilon$-lauroyl-L-lysine solution has been used up, the slurry is filtered, washed with distilled water until the filtrate tested free of chloride, and dried at 95° C. for 4 hours.

The product was sieved through a 60 mesh screen. The product was evaluated as in Example I and, compared to the original untreated titanium dioxide coated mica product, showed improved tactile and dispersion properties. In addition, the product has a blue interference reflection color which appears somewhat brighter and more lustrous than the original untreated product. The small amount of aluminum hydroxide formed aids in the adhesion of the treatment compound.

Titanium dioxide coated mica pigments showing interference reflection colors, due to the thickness of the $TiO_2$ layers on the mica, can be further enhanced in color effects by laking dyes to the $TiO_2$ surfaces. Such products are described in U.S. Pat. No. 4,968,351, above referred to.

These products have interesting and excellent color properties, but the tactile properties are poor. The treatment with N$\epsilon$-lauroyl-L-lysine can affect tactile properties, but the post-treatment may cause other undesired effects such as dye bleeding or some loss of color intensity. Therefore, it is preferable to carry out the treatment during the actual laking process for fixing the dye to the $TiO_2$ surface.

Many different dyes can be used for this type product, as disclosed in U.S. Pat. No. 4,968,351, and the laking process can be basically the same for all.

Colorants, e.g., pigments or dyes other than laked dyes, such as carmine, may also be employed.

Treatment of a complex nacreous pigment which is to contain an absorption colorant may require the use of a method which involves the addition of the lauroyl lysine during the process of precipitating the colorant, such as an organic colorant, on the base pigment, as by a laking process of an organic dye. This method may also be advantageous in some cases with other post-coatings of colors, such as carmine or iron blue.

EXAMPLE VIII

Laked Dye Coated Titanium Dioxide Coated Mica Additionally Coated with 3.0% Nε-Lauroyl-L-Lysine For this example, a titanium dioxide coated mica sample with gold interference reflection color was used (35% $TiO_2$ and 65% mica). The dye for laking selected was FD&C Yellow 5 (Tartrazine).

The FD&C Yellow 5 (supplied by Kohnstamm) was prepared as a 0.5 solution by dissolving 10.0 g. of the dye in 2.0 liters of distilled water. The Nε-lauroyl-L-lysine solution was prepared by dissolving 16.5 g. Nε-lauroyl-L-lysine in 550 ml. 3.5% NaOH solution. The laking solution consisted of 20% $AlCl_3.6H_2O$ in distilled water.

500 g. of the substrate pigment described above (Flamenco Gold of The Mearl Corporation) were dispersed in the dye solution described above, at ambient temperature in a 5 liter Morton flask fitted with a stirrer which was rotated at 270 rpm. 200 ml. of the 20% $AlCl_3.6H_2O$ solution were added at 2.0 ml. per minute, maintaining the pH at 5.0±0.1 by the simultaneous addition of the alkaline treatment solution described above. The total addition time was about 100 minutes.

The slurry was then filtered on a 24 cm. diameter Buchner Funnel fitted with No. 2 Whatman filter paper. The filtrate was washed two times, each with 500 ml. portions of distilled water. The washing of the filter cake was continued with 500 ml. portions of distilled water until the filtrate was essentially free of chloride.

The filter cake was dried at 80° C. for 4 hours, and it was then sieved through a 100 mesh screen.

Testing was done as in Example I, and in particular it was noted that the tactile properties were quite smooth and soft and far superior to the same product laked with the same dye, but lacking the treatment with Nε-lauroyl-L-lysine.

EXAMPLE IX

Iron Blue Coated Titanium Dioxide Coated Mica Additionally Treated with 3.0% Nε-Lauroyl-L-Lysine A titanium dioxide coated mica pigment, characterized by an average platelet size of 10 microns, a mica content of 29%, a titanium dioxide coating on the mica consisting of 63% of the pigment, and a post-coating on the titanium dioxide of ferric ferrocyanide, 8% of the total pigment by analysis, was employed. 125 g. of this pigment (Mattina Blue of The Mearl Corporation) are dispersed in 1450 ml. of distilled water in a 3-liter flask fitted with a stirrer and a pH electrode.

360 ml. of an 0.5 normal sodium hydroxide solution containing 1.06% of Nε-lauroyl-L-lysine are added to the stirred dispersion of the pigment at a rate of 5.0 ml. per minute, at ambient temperature.

Concurrently, a solution of 0.50 normal hydrochloric acid solution containing 0.28% $CaCl_2.2H_2O$ is added at such a rate so as to maintain the pH of the pigment dispersion constant at 3.5±0.1, the addition time being 72 minutes. The stirring was continued another 10 minutes, and then the product was filtered, washed with distilled water, dried at 50° C. overnight, and sieved through a 60 mesh screen.

The tactile properties of this treated product were tested and compared with others, including the untreated original product, Mattina Blue. The treated product was distinctly better than the original untreated material.

Dispersion tests, using several different solvents, were carried out. The treated product showed greater hydrophobicity over the untreated product. The determination of the adhesion of the Nε-lauroyl-L-lysine to the substrate pigment was also carried out. The adhesion of the lauroyl lysine treated product was 82%.

In Examples V and IX, above, the colorants (carmine in Example V and ferric ferrocyanide in Example IX) are deposited on the titanium dioxide coated mica pigments prior to the treatment with lauroyl lysine. Alternatively, however, the colorant and the lauroyl lysine can be deposited on the pigments concurrently, e.g., as in Example VIII. The differences in the properties of the final products are minor. The post-treatment method is simpler and more direct. However, in the case of Example VIII, which employs an organic colorant, post treatment with the lauroyl lysine results in an unsatisfactory final product.

The data in Examples I to IX may be summarized as follows:

TABLE I

Rates of Addition of Solid Nε-Lauroyl-L Lysine (LL) Per Unit Weight of Substrate

| Example | Substrate | LL | Addn. Time (min) | LL Concn. % | Rate (mg./g./min.) |
|---|---|---|---|---|---|
| I | 150 g. | 6.0 g. | 120 | 4 | 0.33 |
| II | 200 lb. | 6 lb. | 60 | 3 | 0.50 |
| III | 225 g. | 4.5 g. | 72 | 2 | 0.28 |
| IV | 681 g. | 20.4 g. | 93.5 | 3 | 0.32 |
| V | 681 g. | 21.0 g. | 80 | 3 | 0.38 |
| VI | 100 g. | 3.0 g. | 40 | 3 | 0.75 |
| VII | 100 g. | 3.0 g. | 40 | 3 | 0.75 |
| VIII | 500 g. | 16.5 g. | 100 | 3 | 0.33 |
| IX | 125 g. | 3.8 g. | 72 | 3 | 0.42 |

EXAMPLE X

Comparison Example: Blend of Mica and 3.0% Nε-Lauroyl-L-Lysine, Compared to Coating on Mica 4.00 g. of wet ground Indian mica, average platelet size of 10 microns (same as used in Example II) were placed in a 2 oz. glass jar. 0.12 g. of Nε-lauroyl-L-lysine powder were added along with 4 steel shots, the jar capped and placed on a roller for 30 minutes.

The jar was then removed from the roller, and the 4 steel shots were separated from the pigment. The tactile properties were determined in comparison with other samples. The product of this experiment was much poorer than that of Example II, and it was only somewhat better than that of the untreated mica.

The determination of adhesion of the treatment compound to the substrate pigment was carried out, and it was found to be 21%. This is quite unsatisfactory compared to treatment procedures of this invention, yielding adhesions of at least 80% in most cases, and not less than 60%.

EXAMPLE XI

Variation of Addition Rates of Nε-Lauroyl-L-Lysine to Mica Substrate 100 g. of wet ground Indian mica, average platelet size of 10 microns, were dispersed in 400 ml of distilled water at room temperature. 300 ml of 0.5 normal sodium hydroxide solution were prepared containing 1.0% Nε-lauroyl-L-lysine. This solution was added at a particular rate to the mica dispersion in each of the following experiments, holding the pH constant at 3.0±0.1 by the concurrent addition of 0.50 normal HCl solution. The rates of addition of the NaOH solution containing 1.0% Nε-lauroyl-L-lysine, and the results are given in the following table:

| Expt. | Addn. Rate of NaOH Soln. (ml/min) | Addn. Time (min) | Addn. Rate, Mg. Lauroyl Lysine/g mica/min | Tactile Rank | Tactile Rating | Pct. of Cmpd. Adhered |
|---|---|---|---|---|---|---|
| A | 4.0 | 25 | 1.2 | 3 | Good- | 97 |
| B | 3.0 | 33 | 0.9 | 1 | Good | 93 |
| C | 2.0 | 50 | 0.6 | 2 | Good | 96 |
| D (Std at pH 6) | 2.2 | — | — | 4 | — | — |
| E (Mica) | — | — | — | 5 | — | — |

Room temperature was used. The addition rate is that of the 0.5 normal NaOH solution containing 1.0% Nε-lauroyl-L-lysine to the mica slurry. The actual addition rates of the treatment compared to the substrate are 0.4, 0.3, and 0.2 mg/g/min.

EXAMPLE XII

Variation of Addition Rates of Nε-Lauroyl-L-Lysine to Titanium Dioxide Coated Mica Pigment Substrate Titanium dioxide coated mica characterized by an average platelet size of 18 microns, an analysis of 46% TiO$_2$ and 56% mica, and an interference reflection color of blue, was used. 100 g. of this pigment (Flamenco Blue of The Mearl Corporation) were dispersed in 600 ml. of distilled water. 100 ml. of 3.5% NaOH solution containing 3.0% Nε-lauroyl-L-lysine were added, at different rates in each experiment. The pH was maintained at 6.0±0.1 by the concurrent addition of 0.5 normal HCl solution. The particular rates used in the several procedures are given in the following table, along with the results. Room temperature was used.

| Expt. | Addn. Rate of NaOH Soln. (ml/min) | Addn. Time (min) | Addn. Rate, Mg. Lauroyl Lysine/g mica/min | Tactile Rank | Tactile Rating | Pct. of Cmpd. Adhered |
|---|---|---|---|---|---|---|
| A | 0.5 | 200 | 0.15 | 2 | Good | 93 |
| B | 1.0 | 100 | 0.30 | 3 | Good | 96 |
| C | 4.0 | 25 | 1.2 | 1 | Good | 87 |
| D(Std[1]) | — | — | — | 1 | — | — |
| E (Untreated Pigment) | — | — | — | 4 | — | — |

[1]Standard is same pigment treated with 2% lecithin.

The addition rate is that of the 0.5 normal NaOH solution containing 1.0% Nε-lauroyl-L-lysine to the pigment slurry. The actual rates of addition of the treatment with respect to the substrate are 0.15, 0.30, and 1.20 mg./g./min.

The limitations on the particular post-treatment method are predicated upon attaining a final platy pigment product that has improved tactile properties, shows evidence of good adhesion of the lauroyl lysine to the pigment surface substrate, and demonstrates improved dispersion behavior of the treated pigment compared to the untreated pigment. This improvement is generally in the direction of greater hydrophobic character. The lauroyl lysine crystalline solid surface has both hydrophilic and hydrophobic character, and in a sense the lauroyl lysine partially replaces the substrate surface hydrophile-hydrophobe character for its own. Thus, treated mica is more hydrophobic than untreated mica.

The tactile properties are evaluated by spreading the powder on the skin and judging the smoothness and lack of drag, compared to standard materials. These evaluations are commonly carried out by experienced people in laboratories of cosmetic formulating firms.

As indicated above, in determining the adhesion of the coating to the substrate, four successive centrifugations are carried out. The conditions of the centrifugation are not critical so long as effective separation of the solid (settled) and liquid (supernatant) phases are achieved. The following procedure may suitably be employed:

To 75 ml. of distilled water is added 1.00 g. of the powder sample and dispersed in a 150 ml Corex centrifuge tube, No. 1265 (Catalog No. 21025-065 of VWR Scientific). Care must be taken to thoroughly disperse the sample, which can be done by vibratory or ultrasonic techniques usually available in laboratories. Centrifugation is carried out for 20 minutes, using a Servall refrigerated centrifuge fitted with the large head. The effective radius is 5.75 inches, and for a speed of 7200 rpm, the force field is about 8440×g (g=gravitational constant).

A high force field is desirable so as to obtain a clean separation of the liquid floating the non-adherent lauroyl lysine from the pigment particles, and the latter preferably should pack hard on the bottom of the tube, which facilitates the separation of the solid powder and liquid phases by decanting the latter.

Lesser force fields can be used, so long as they enable effective separation of the solid settled and liquid supernatant phases.

The supernatant liquid is decanted and saved, and the settled solid is redispersed in an equal volume of distilled water, and centrifugation is repeated. After four centrifugations are carried out in this way, the supernatant liquids are combined and analyzed for the treatment compound that was removed. Alternatively, the settled paste of the powder can be analyzed.

Generally, the amount of treatment compound that adheres to a mica substrate in the products of this invention is at least 80% and often over 90%. For other pigment substrates at least 80% adhesion is desired, and at least 60% is acceptable. The platy pigments of this invention all have at least 60% adhesion.

Evaluation of the dispersion properties is done so as to determine the shift in hydrophilic-hydrophobic character with the added treatment of the pigment. 2.0 g. of treated or untreated mica (1.50 g. of other substrates) are dispersed in 100 ml of each solvent in a graduated centrifuge tube, shaken, and allowed to settle. The tubes are observed at 30 min., 60 min., and 120 min. The centrifuge tube is Corning 8160 (Thomas Scientific 2622-D40) of 100 ml with graduations on a red glass layer, and measures about 7¾ inch in length and about 1½-inch in outside diameter at the midpoint in height.

The solvents usually used are distilled water, isopropanol, butyl acetate, and toluene. After two hours, two observations are recorded for each tube, settled volume of the powder, and appearance (clarity or haziness) of the supernatant liquid. The tests are done with the untreated pigments for comparison.

Hydrophobic behavior is shown by high volume of the powder and clarity of the supernatant liquid in water along with low volume of powder and haziness of the supernatant liquid in toluene. For hydrophilic behavior the two solvents are reversed; the behavior in the two other solvents is intermediate. In general, but not necessarily always, the hydrophilic-hydrophobic is shifted towards the latter.

The extent of the shift towards hydrophobicity varies with the substrate pigments. This test is generally significant because it indicates whether or not the substrate pigment has been adequately treated by the lauroyl lysine.

The platy pigments of this invention may be advantageously employed in eye shadow compositions, such as pressed powder eye shadow in a wide range of proportions. Useful ranges of proportions of components in such compositions are listed in the following table, the pigments exemplified being treated before formulation with a compound of the general formula shown above:

TABLE II

| | Proportions, weight % | |
|---|---|---|
| Component | Matte Comp. (Low Luster) | Frosted Comp. (High Luster) |
| Talc | 5–70 | 5–70 |
| Zinc Stearate | 2–10 | 2–10 |
| Iron Oxides | 3–10 | — |
| Mica, wet ground, 10 microns avg. size | 5–70 | — |
| Flamenco Blue[1] titanium dioxide coated mica | — | 25–70 |
| Mineral Oil | 2–7 | 2–7 |
| Isopropyl Myristate | 2–7 | — |
| 2-Ethyl-Hexyl Palmitate | — | 2–7 |

[1]Mearl Corporation Flamenco Blue, showing a blue interference reflection color and having an average composition of 46% TiO$_2$ and 54% mica (average particle size of 20 microns).

The following are examples of eye shadow compositions of this invention:

EXAMPLE XIII

| Matte (Low Lustre) Pressed Powder Eye Shadow | |
|---|---|
| Component | Weight % |
| Talc | 30 |
| Zinc Stearate | 3 |
| Iron Oxides | 5 |
| Mica, wet ground, 10 microns avg. size | 50 |
| Mineral Oil | 6 |
| Isopropyl Myristate | 6 |

The talc and the mica were treated before formulation with Nε-lauroyl-L-lysine. This formulation has superior tactile properties on the skin compared to the same formulation containing untreated talc and untreated mica.

EXAMPLE XIV

| Frosted (high luster) Pressed Powder Eye Shadow | |
|---|---|
| Component | Weight % |
| Talc | 25 |
| Zinc Stearate | 8 |
| Flamenco Blue | 60 |
| titanium dioxide coated mica | |
| Mineral Oil | 3 |
| 2-Ethyl-Hexyl Palmitate | 4 |

The talc and titanium dioxide coated mica pigment were treated before formulation with Nε-lauroyl-L-lysine. This formulation has superior tactile properties in testing compared to the same formulation containing untreated talc and untreated platy pigment.

While certain representative embodiments and details have been shown for the purpose of illustrating the invention, it will be apparent to those skilled in the art that various changes may be made therein without departing from the spirit or scope of the invention.

What is claimed is:

1. A process for improving the tactile characteristics of a platy pigment comprising precipitating a compound of the general formula

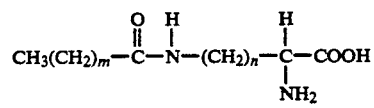

where m is an even number from 8 to 18 and n is 3 or 4, onto the surface of said platy pigment, said precipitation being accomplished by adding an acid or alkaline solution of said compound to an aqueous dispersion of said platy pigment, the amount of said solution being such as to supply said compound in an amount of about 0.5–5.0% by weight of said platy pigment, while maintaining the temperature between about 15° and 80° C., said acid or alkaline solution being added at a rate not exceeding 1.50 mg of said compound per gram of platy pigment per minute, adding alkali or acid as required to bring the pH of the resulting mixture to between 1 and 8, and recovering said platy pigment coated with said compound.

2. A process as defined in claim 1 wherein the compound of said general formula is entirely either the D or L isomer.

3. A process as defined in claim 2 wherein said pH of the resulting mixture is brought to about 2.5–5.0.

4. A process as defined in claim 1 wherein the compound of said general formula is Nε-lauroyl-L-lysine.

5. A process as defined in claim 2 wherein the compound of said general formula is precipitated onto the surface of said platy pigment in the presence of a calcium salt.

6. A process as defined in claim 5 wherein said calcium salt is calcium chloride and 0.25–1.0 mole of said calcium chloride is present per mole of the compound of said general formula.

7. A process as defined in claim 2 wherein said platy pigment is mica and said mica is present in said aqueous dispersion in a concentration in the range of about 4–24% on a wt./wt. basis.

8. A process as defined in claim 2 wherein said platy pigment is iron oxide coated mica and said iron oxide coated mica is treated with a polyvalent metal compound before or during the addition of the compound of said general formula, said polyvalent metal compound being a hydroxide or a compound hydrolyzable to a hydroxide.

9. A process as defined in claim 8 wherein said polyvalent metal compound is ferric chloride.

10. A process as defined in claim 2 wherein said platy pigment is titanium dioxide coated mica and said titanium dioxide coated mica is treated with a polyvalent metal compound before or during the addition of the compound of said general formula, said polyvalent metal compound being a hydroxide or a compound hydrolyzable to a hydroxide.

11. A process as defined in claim 10 wherein said polyvalent metal compound is aluminum chloride.

12. A process as defined in claim 2 wherein said platy pigment is chromium (III) oxide coated mica and said chromium oxide mica is treated with a polyvalent metal compound before or during the addition of the compound of said general formula, said polyvalent metal compound being a hydroxide or a compound hydrolyzable to a hydroxide.

13. A process as defined in claim 12 wherein said polyvalent metal compound is chromium (III) chloride or sulfate.

14. A process as defined in claim 2 wherein said platy pigment is titanium dioxide coated mica, said titanium dioxide being coated with a dye or pigment.

15. A process as defined in claim 16 wherein said dye or pigment is carmine or a laked dye.

16. A process as defined in claim 14 wherein said dye or pigment is ferric ferrocyanide.

17. A process as defined in claim 2 wherein said platy pigment is titanium dioxide coated mica and an organic colorant is deposited on the titanium dioxide concurrently with the compound of said general formula.

18. A process as defined in claim 2 wherein the coated platy pigment is recovered by allowing it to settle, washing it, concentrating it by centrifuging or filtration and then drying it.

19. A process as defined in claim 2 wherein said platy pigment is talc and said talc is present in said aqueous dispersion in a concentration in the range of about 5%-15% on a wt./wt. basis.

20. A platy pigment product produced by a process as defined in claim 2.

21. A platy pigment having improved tactile, dispersion, and stability properties, said pigment comprising a substrate of platelets of mica, talc, or a metal oxide coated mica, said substrate being coated with Nε-lauroyl-L-lysine, said platelets having a particle size in the range of about 2-80 microns, with the average particle size in the range of about 5-40 microns, the Nε-lauroyl-L-lysine coating being present on the surface of said platelets in the range of about 0.5% to 5.0% by weight of the platelets, and at least 80% of said coating remaining adhered to said substrate after four centrifugations in distilled water, each centrifugation being carried out on a dispersion of 1.00 g. of said platy pigment in 75 ml. of distilled water.

22. A platy pigment according to claim 21 wherein said substrate is mica.

23. A platy pigment according to claim 21 wherein said substrate is iron oxide coated mica.

24. A platy pigment according to claim 21 wherein said substrate is titanium dioxide coated mica.

25. A platy pigment according to claim 21 wherein said substrate is chromium (III) oxide coated mica.

26. A platy pigment according to claim 21 wherein said substrate is titanium dioxide coated mica, said titanium dioxide being coated with a dye or pigment.

27. A platy pigment according to claim 26 wherein said dye or pigment is carmine or a laked dye.

28. A platy pigment according to claim 26 wherein said dye or pigment is ferric ferrocyanide.

29. A platy pigment according to claim 21 wherein said substrate is titanium dioxide coated mica and said substrate is coated with a concurrent deposit of an organic colorant and said Nε-lauroyl-L-lysine.

30. A platy pigment according to claim 21 wherein said substrate is talc.

31. A cosmetic composition containing a platy pigment product produced by the process defined in claim 1 in combination with cosmetically acceptable ingredients.

32. An eye shadow composition containing a platy pigment produced by the process defined in claim 1 in combination with cosmetically acceptable ingredients.

33. An eyeshadow composition containing a platy pigment produced by the process defined in claim 4 in combination with cosmetically acceptable ingredients.

34. A matte pressed powder eye shadow composition comprising, by weight:

| Talc | 5-70% |
| --- | --- |
| Zinc Stearate | 2-10% |
| Iron Oxides | 3-10% |
| Mica, wet ground, 10 microns avg. size | 5-70% |
| Mineral Oil | 2-7% |
| Isopropyl Myristate | 2-7% | in which the talc and the mica are treated before formulation with Nε-lauroyl-L-lysine by the process of claim 1.

35. A frosted pressed powder eye shadow composition comprising by weight:

| Talc | 5-70% |
| --- | --- |
| Zinc Stearate | 2-10% |
| Flamenco Blue titanium dioxide coated mica | 25-70% |
| Mineral Oil | 2-7% |
| 2-Ethyl-Hexyl Palmitate | 2-7% | in which the Flamenco Blue shows a blue interference reflection color and has an average composition of 46% $TiO_2$ and 54% mica and an average particle size of 20 microns, and the talc and the titanium dioxide coated mica pigments are treated before formulation with Nε-lauroyl-L-lysine by the process of claim 1.

36. A process as defined in claim 1 wherein said acid or alkaline solution is added at a rate within the range of about 0.10-1.50 mg. of said compound per gram of platy pigment per minute.

* * * * *